United States Patent
Schelling et al.

(10) Patent No.: US 8,841,480 B2
(45) Date of Patent: Sep. 23, 2014

(54) PROCESS FOR THE PREPARATION OF LIGHT-COLORED IOCYANATES OF A DIPHENYLMETHANEDIISOCYANATE SERIES

(75) Inventors: Heiner Schelling, Kirchheim (DE); Hans-Juergen Pallasch, Kallstadt (DE); Eckhard Stroefer, Mannheim (DE); Jon S. Speier, Baton Rouge, LA (US); Byoung-Yeon Kim, Baton Rouge, LA (US)

(73) Assignee: BASF SE, Ludwigshafen (DE)

( * ) Notice: Subject to any disclaimer, the term of this patent is extended or adjusted under 35 U.S.C. 154(b) by 99 days.

(21) Appl. No.: 13/383,549

(22) PCT Filed: Jul. 15, 2010

(86) PCT No.: PCT/EP2010/060237
§ 371 (c)(1),
(2), (4) Date: Jan. 11, 2012

(87) PCT Pub. No.: WO2011/006970
PCT Pub. Date: Jan. 20, 2011

(65) Prior Publication Data
US 2012/0108843 A1 May 3, 2012

Related U.S. Application Data

(60) Provisional application No. 61/226,101, filed on Jul. 16, 2009.

(51) Int. Cl.
*C07C 263/00* (2006.01)
*C08G 18/76* (2006.01)
*C01B 31/28* (2006.01)
*C07C 263/10* (2006.01)

(52) U.S. Cl.
CPC ............ *C01B 31/28* (2013.01); *C08G 18/7664* (2013.01); *C07C 263/10* (2013.01)
USPC ........................................................ 560/347

(58) Field of Classification Search
None
See application file for complete search history.

(56) References Cited

U.S. PATENT DOCUMENTS 2,733,254 A 1/1956 Allen et al.
4,465,639 A 8/1984 Hatfield, Jr.
(Continued)

FOREIGN PATENT DOCUMENTS

| EP | 0 133 538 | 2/1985 |
| EP | 0 546 398 | 6/1993 |
| WO | 2009 013303 | 1/2009 |

OTHER PUBLICATIONS

U.S. Appl. No. 13/266,049, filed Oct. 24, 2011, Stroefer, et al.
(Continued)

*Primary Examiner* — Karl J Puttlitz
(74) *Attorney, Agent, or Firm* — Oblon, Spivak, McClelland, Maier & Neustadt, L.L.P.

(57) ABSTRACT

The present invention accordingly provides a process for preparing light-colored polyphenylene-polymethylene polyisocyanates comprising the steps (a) providing an amount of chlorine, (b) separating the chlorine provided in the step (a) to obtain a first chlorine fraction having a content of free and bound bromine and iodine of <50 ppm and a second chlorine fraction having an increased content of free and bound bromine and iodine that depends on the original amount of bromine and iodine in the chlorine provided in step (a) and the separation split, (c) reacting carbon monoxide with at least a portion of the first chlorine fraction to form a first phosgene fraction, (d) reacting carbon monoxide with at least a part of the second chlorine fraction to form a second phosgene fraction, (e) reacting at least a portion of a first phosgene fraction with at least one amine of the diphenylmethane diamine series (MDA) to form the corresponding polyphenylene-polymethylene polyisocyanate (PMDI), and (f) reacting at least a portion of the second phosgene fraction with at least one primary amine with the exception of mono- and polyphenylene-polymethylene polyamines to form an at least one isocyanate-containing reaction solution.

6 Claims, 1 Drawing Sheet

(56) References Cited

U.S. PATENT DOCUMENTS

| | | |
|---|---|---|
| 5,364,958 A | 11/1994 | Ishida et al. |
| 2004/0024244 A1* | 2/2004 | Walsdorff et al. ............ 560/347 |
| 2010/0217035 A1 | 8/2010 | Knoesche et al. |
| 2011/0124908 A1 | 5/2011 | Rumpf et al. |
| 2011/0251425 A1 | 10/2011 | Penzel et al. |
| 2011/0263892 A1 | 10/2011 | Breuninger et al. |
| 2011/0269995 A1 | 11/2011 | Olbert et al. |
| 2011/0288334 A1 | 11/2011 | Olbert et al. |
| 2011/0313192 A1 | 12/2011 | Rosendahl et al. |
| 2011/0319662 A1 | 12/2011 | Olbert et al. |
| 2012/0004446 A1 | 1/2012 | Mattke et al. |

OTHER PUBLICATIONS

U.S. Appl. No. 61/220,740, filed Jun. 26, 2009, Schelling, et al.
U.S. Appl. No. 13/380,680, filed Dec. 23, 2011, Schelling, et al.
U.S. Appl. No. 61/225,376, filed Jul. 14, 2009, Schelling, et al.
U.S. Appl. No. 13/383,433, filed Jan. 11, 2012, Schelling, et al.
U.S. Appl. No. 13/479,961, filed May 24, 2012, Stroefer, et al.
International Search Report Issued Nov. 24, 2010 in PCT/EP10/60237 Filed Jul. 15, 2010.
U.S. Appl. No. 13/434,135, filed Mar. 29, 2012, Lehr, et al.

* cited by examiner

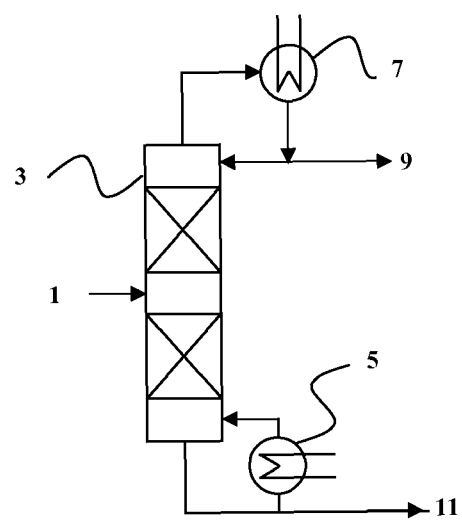

PROCESS FOR THE PREPARATION OF LIGHT-COLORED IOCYANATES OF A DIPHENYLMETHANEDIISOCYANATE SERIES

Isocyanates and isocyanate mixtures are prepared by known methods by phosgenation of the corresponding amines. For polyurethane foams, use is made, for example of bifunctional or polyfunctional aromatic isocyanates of the diphenylmethane diisocyanate series (MDI). Due to the preparation process, the phosgenation and subsequent workup (removal of the solvent; separation of monomeric MDI) often results in dark-colored products, which in turn give yellowish polyurethane foams or other likewise discolored PUR materials. This is undesirable, since such discoloration adversely effects the overall visual impression and allows slight inhomogeneities to occur, e.g. as streaks in the foams obtained. Light-colored isocyanates or isocyanates which contain a reduced amount of color-imparting components are therefore preferred as raw materials.

There have always been many attempts to obtain polyisocyanates, in particular the ones of the diphenylmethane diisocyanate series, having a light color. Numerous methods are known for empirically lightening the color of MDI. However, the nature of the troublesome color substances has hitherto been elucidated only to an unsatisfying degree.

The previously known methods can be divided into four groups:

1. Processes in which the starting material diaminodiphenylmethane (MDA) or its oligomers have been subjected to treatment and/or purification.

EP-A10546398 describes a process for preparing polymeric MDI in which the polymethylene-polyphenylene-polyamine used as starting material is acidified prior to phosgenation. The abovementioned method gives only a slight improvement of the color, since the color substances in the MDI have been found on the basis of experience to be formed not only from certain MDI secondary components but also to result from color precursors which are formed by secondary reactions during the phosgenation.

2. Process engineering solutions in the phosgenation process

U.S. Pat. No. 5,364,958 relates to a process for preparing polyisocyanates in which, after the phosgenation, the phosgene is removed completely at low temperature and diisocyanate is subsequently treated with hot HCl gas. Although processes of this type attempt to remove discoloring components at the correct point, this process is not efficient enough, both because of its high engineering outlay and the high costs and also in terms of its color-lightening effect, since only slight degradation of color precursors occurs due to incomplete chemical reactions.

3. Addition of color-lightening additives to the crude isocyanate product obtained after the phosgenation and before the workup.

According to U.S. Pat. No. 4,465,639, water is added to the crude product obtained after the phosgenation in order to lighten its color. Although the above-described method of lightening the color is efficient, it has disadvantages and the additives not only lighten the color, but also undergo reactions with the isocyanates obtained as products, generally resulting, for example, in an undesired reduction of the isocyanate content. In addition, there is the risk of formation of undesired by-products in the MDI.

4. After treatment of the end-product

EP-A1 013 3538 describes the purification of isocyanates by extraction, giving fractions of light-coloured MDI. This colour-improving after-treatment of the isocyanate end products after complete removal of the solvent at elevated temperature is likewise not very efficient, since the high temperatures occurring during the workup, in particular during the distillation of the solvent and (in the case of the preparation of polymeric MDI) the removal of monomeric MDI have already resulted in the formation of stable colored substances which can be chemically degraded only with difficulty.

It is an object of the present invention to provide a new process for preparing isocyanates which contain no or only small amounts of color-imparting discolouring components. A further object of the invention is to provide a process for preparing isocyanates that, without the above-mentioned treatment steps, leads to light-coloured isocyanates which are suitable for producing polyurethanes or their precursors which have no color or only a slight color.

The present invention accordingly provides a process for preparing light-coloured polyphenylene-polymethylene polyisocyanates (PMDI) comprising the steps of (a) providing an amount of chlorine, having a certain content of bromine and iodine, (b) separating the chlorine provided in the step (a) to obtain a first chlorine fraction having a content of free and bound bromine and iodine of <50 ppm and a second chlorine fraction having an increased content of free and bound bromine and iodine that depends on the original amount of bromine and iodine in the chlorine provided in step (a) and the separation split, (c) reacting carbon monoxide with at least a portion of the first chlorine fraction to form a first phosgene fraction, (d) reacting carbon monoxide with at least a part of the second chlorine fraction to form a second phosgene fraction, (e) reacting at least a portion of a first phosgene fraction with at least one amine of the diphenylmethane diamine series (MDA) to form the corresponding polyphenylene-polymethylene polyisocyanate (PMDI), and (f) reacting at least a portion of the second phosgene fraction with at least one primary amine with the exception of mono- and polyphenylene-polymethylene polyamines to form an at least one isocyanate-containing reaction solution.

Step (e) of the process of the present invention leads to isocyanates of the polyphenylene-polymethylene group (PMDI) which, if desired even without the above-described additional treatments, can be used for preparing urethane compounds such as polyurethanes or their precursors which have no colour or only a slight colour.

Furthermore, the process of the invention has the advantage that the bromine-rich second chlorine fraction obtained in step (b) is used for the synthesis of further isocyanates. The isocyanates obtained in the reaction of step (f) of the inventive process can be treated according to the above-described treatments.

For the purpose of the present invention, bromine and iodine in molecular form means molecules which consist entirely of bromine or iodine atoms. Bromine and iodine in bound form means molecules which comprise not only bromine or iodine but also atoms different from the specified atoms.

The phosgene used for the preparation of isocyanates generally has a certain content of molecular or bound bromine or iodine or both. The content of bromine or iodine in the phosgene results from the chlorine used for preparing the phosgene, since the chlorine usually contains a certain proportion of bromine or iodine or both. The content of bromine and iodine or both in the chlorine generally results from the corresponding content in the salt used for producing the chlorine. The bromine or the BrCl present in the chlorine leads to formation of dibromophosgene or bromochlorophosgene in the phosgene-synthesis. These compounds are said to react similarly to phosgene with amines to form isocyanates and hydrogen bromide (U.S. Pat. No. 2,733,254). Analogous reactions may be assumed for iodine.

Methods of preparing and providing chlorine are known to those skilled in the art. In principle, the present invention can be carried out using any chlorine which contains less than 1000 ppm of bromine or iodine or both in molecular and/or bound from i.e.: molecular bromine or bromine compounds alone, molecular iodine or iodine compounds alone, both molecular bromine and iodine, molecular bromine and iodine as well as bromine compounds, molecular bromine and iodine as well as iodine compounds, bromine compounds and iodine compounds, or molecular bromine and iodine as well as bromine compounds and iodine compounds.

Methods of preparing suitable chlorine are known to those skilled in the art. In principle it is possible to use any chlorine which meets the above-mentioned specification, i.e. which contains less than about 1000 ppm of bromine and iodine. Thus, for example, it is possible to use chlorine which has been produced by electrolysis processes or by oxidation of hydrogen chloride, e.g. by the Deacon process, as long as the hydrogen chloride used also has a sufficiently low bromine and iodine content.

According to an embodiment of the invention, the chlorine is produced by electrolysis of the solution containing chloride ions. In general, this is an aqueous rock salt solution, an aqueous potassium chloride solution or aqueous hydrogen chloride (hydrochloric acid). Thus, the chlorine synthesis can be carried out using appropriate starting materials which themselves have a little bromine or iodine content, e.g. low bromine and low iodine salts, or low-bromine and low-iodine hydrochloric acid. Such low bromine and low iodine salts having a total bromine and iodine content of <1000 ppm are mined, for example, at Heilbronn, Germany.

In step (b) of the process of the invention, the chlorine provided in step (a) is separated into two fractions, preferably by means of distillation, to obtain a first chlorine fraction having a content of free and bound bromine and iodine of less than 50 ppm, or less than 40 ppm or less than 25 ppm, in particular of 10 ppm or less; and a second chlorine fraction having an increased content of free and bound bromine and iodine. The increased content of bromine and iodine in the second chlorine fraction depends on the original amount of bromine and iodine in the chlorine and the separation split.

In steps (c) and (d) the first and second chlorine fraction are reacted with carbon monoxide to form a first phosgene fraction having a content of bromine and iodine in molecular and/or bound form of less than 50 ppm, a second phosgene fraction having a higher content of bromine and iodine in molecular and/or bound form, respectively. Methods of preparing phosgene are e.g. described in Ullmanns Enzyklopädie der Industriellen Chemie, 3$^{rd}$ edition, volume 13, pages 494 to 500. Thus, phosgene can be obtained by passing carbon monoxide and chlorine over activated carbon.

In step (e) at least a portion of the first phosgene fraction having a content of bromine and iodine in molecular or bound form of less than 50 ppm is reacted with the at least one polyphenylene-polymethylene polyamine to form the corresponding polyphenylene-polymethylene polyisocyanate (PMDI) and hydrogen chloride.

In step (f) at least a portion of the second phosgene fraction having a content of bromine and iodine in molecular or bound form of more than 50 ppm is reacted with at least one primary amine with the exception of mono- and polyphenylene-polymethylene polyamines to form the corresponding isocyanates and hydrogen chloride. The amines used in step (f) of the method of the invention have at least one primary amino group, preferably two primary amino groups and possibly also three or more primary amino groups.

The preparation of isocyanates taking place in steps (e) and (f) in the process of the present invention is carried out in a manner known to those skilled in the art by reacting an amine or a mixture of two or more amines with a super-stoichiometric amount of phosgene. It is in principle possible to employ all methods in which a primary amine or a mixture of two or more primary amines is reacted with phosgene to form one or more isocyanate groups.

According to a preferred embodiment of the invention, the process of reacting the amines or the mixture of two or more amines with phosgene is carried out in a solvent or mixture of two or more solvents.

As solvent it is possible to use all solvents suitable for the preparation of isocyanates. Preferred are inert aromatic, aliphatic or alicyclic hydrocarbons or their halogenated derivatives. Examples of such solvents are aromatic compounds such as monochlorobenzene or dichlorobenzene, for example o-dichlorobenzene, toluene, xylenes, naphthalene derivatives such as tetralin or decalin, alkanes having from about 5 to about 12 carbon atoms, e.g. hexane, heptane, octane or decane, cycloalkanes such as cyclohexane, inert esters and inert ethers such as ethyl acetate or butyl acetate, tetrahydrofuran, dioxane or diphenyl ether.

According to the present invention the amine reacted in step (e) is an amine of the diphenylmethanediamine series or mixture of two or more such amines. According to this embodiment of the invention the amines used are the isomeric primary diphenylmethanediamines (MDA) or their oligomeric or polymeric derivatives, i.e. diamines of a diphenylmethanediamine series. Diphenylmethanediamine, its oligomers or polymers are obtained, for example, by condensation of aniline with formaldehyde. Such oligoamines or polyamines or mixtures thereof are also used in a preferred embodiment of the invention.

The amines reacted in step (f) of the present invention are in principle all linear or branched, saturated or unsaturated aliphatic or cycloaliphatic or aromatic primary amines, provided that they can be converted into isocyanates by means of phosgene, provided that the isomeric, primary diphenylmethanediamines (MDA) or their oligomeric or polymeric derivatives, i.e. the amines of the diphenylmethanediamine series are excluded. Examples of suitable amines are 1,3-propylenediamine, 1,4-butylenediamine, 1,5-pentamethylenediamine, 1,6-hexamethylenediamine and the corresponding higher homologues of this series, isophoronediamine (IPDA), cyclohexyldiamine, cyclohexylamine, aniline, phenylenediamine, p-toluidine, 1,5-naphthylenediamine, 2,4- or 2,6-toluenediamine or mixtures thereof.

After going through steps (e) and (f) of the process of the present invention, the above-mentioned compounds are in the form of the corresponding isocyanate. Light-colored isocyanates of the diphenylmethanediisocyanate series can be prepared by the process of the present invention. In step (e) isocyanates with maybe increased bromine and/or iodine content are prepared. These isocyanates can be subjected to purification and/or treatment by one or more of the methods 1 to 4 described beforehand.

The reactions in steps (e) and (f) can be carried out continuously or batchwise in one or more stages. If a single-stage reaction is carried out, this reaction preferably takes place at from about 60 to 200° C., for example at from about 130 to 180° C.

According to a preferred embodiment of the invention, the reaction in steps (e) and (f) is carried out in two stages.

During the reaction in step (e) and/or (f) superatmospheric pressure can be applied, for example up to about 100 bar or less, preferably from about 1 bar to about 50 bar or from about 2 bar to about 25 bar or from about 3 bar to about 12 bar. However, the reaction can also be carried out under atmospheric pressure. In a further preferred embodiment of the invention, the reaction is accordingly carried out at ambient pressure, generally about 1 bar. In a further preferred embodiment, the reaction can also be carried out at a pressure below ambient pressure.

Excess phosgene is preferably removed at from about 50 to 180° C. after the reaction of step (e) and/or (f). The removal of remaining traces of solvent is preferably carried out under reduced pressure, for example the pressure should be about 500 mbar or less, preferably less than 100 mbar. In general, the various components are separated off in the order of their boiling points; it is also possible to separate off mixtures of various components in a single process step.

The process of the present invention is explained in more detail below with reference to the figures by way of the examples.

In FIG. 1, the first stream of chlorine 1 corresponding to 10 tons per hour having a content of free and bound bromine and iodine of 250 ppm is fed into a distillation column 3 equipped with a reboiler 5 and a condenser 7. In the distillation column 3 the stream of chlorine 1 is then separated in a first chlorine fraction 9 corresponding to 5 tons per hour having a content of free and bound bromine and iodine of 10 ppm, and a second chlorine fraction 11 corresponding to 5 tons per hour having a content of free and bound bromine and iodine of 490 ppm. In subsequent reaction steps at least a portion of the first chlorine fraction 9 is used for the synthesis of polymeric MDI. At least a portion of the second chlorine fraction 11 is used for the preparation of isocyanates with possibly increased bromine and/or iodine content, which can be subjected to purification and/or treatment by one or more of the methods described beforehand.

The invention claimed is:

1. A process for preparing a polyphenylene-polymethylene polyisocyanate (PMDI), the process comprising
    (a) separating an amount of chlorine, having an original amount of bromine and iodine, to obtain a first chlorine fraction having a content of free and bound bromine and iodine of less than 50 ppm and a second chlorine fraction having an increased content of free and bound bromine and iodine that depends on the original amount of bromine and iodine and a separation split,
    (b) reacting carbon monoxide with at least a portion of the first chlorine fraction to form a first phosgene fraction,
    (c) reacting carbon monoxide with at least a portion of the second chlorine fraction to form a second phosgene fraction,
    (d) reacting at least a portion of the first phosgene fraction with at least one amine of a diphenylmethane diamine (MDA) to form a polyphenylene-polymethylene polyisocyanate (PMDI), and
    (e) reacting at least a portion of the second phosgene fraction with at least one primary amine to form an isocyanate, wherein the primary amine is selected from the group consisting of 1,3-polyphenylenediamine, 1,4-butylenediamine, 1,5-pentamethylenediamine, 1,6-hexamethylenediamine, a methylenediamine homologue of 1,7-heptamethylene diamine or higher, isophoronediamine (IPDA), cyclohexyldiamine, cyclohexylamine, aniline, phenylenediamine, para-toluidine, 1,5-naphthylenediamine, 2,4-toluenediamine, and 2,6-toluenediamine, provided that mono-and polyphenylene polymethylene poly-amines are excluded.

2. The process of claim 1, wherein the reacting of the first phosgene fraction (d), the reacting of the second phosgene fraction (e), or both the reacting (d) and the reacting (e), is carried out in a solvent.

3. The process of claim 2, wherein the solvent is at least one selected from the group consisting of o-dichlorobenzene, toluene, xylene, tetralin, decalin, hexane, heptane, octane, decane, cyclohexane, ethyl acetate, butyl acetate, tetrahydrofuran, dioxane and diphenyl ether.

4. The process of claim 1, wherein the reacting of the first phosgene fraction (d), the reacting of the second phosgene fraction (e), or both the reacting (d) and reacting (e), is carried out under superatmospheric or atmospheric pressure.

5. The process of claim 2, wherein the reacting of the first phosgene fraction (d), the reacting of the second phosgene fraction (e), or both the reacting (d) and the reacting (e), is carried out under superatmospheric or atmospheric pressure.

6. The process of claim 3, wherein the reacting of the first phosgene fraction (d), the reacting of the second phosgene fraction (e), or both the reacting (d) and the reacting (e), is carried out under superatmospheric or atmospheric pressure.

* * * * *

UNITED STATES PATENT AND TRADEMARK OFFICE
CERTIFICATE OF CORRECTION

PATENT NO. : 8,841,480 B2  
APPLICATION NO. : 13/383549  
DATED : September 23, 2014  
INVENTOR(S) : Heiner Schelling et al.

Page 1 of 1

It is certified that error appears in the above-identified patent and that said Letters Patent is hereby corrected as shown below:

On the title page, Item (54) and in the specification, Column 1, the title information is incorrect. Item (54) and Column 1 should read:

-- PROCESS FOR THE PREPARATION OF LIGHT-COLORED ISOCYANATES OF A DIPHENYLMETHANEDIISOCYANATE SERIES --

Signed and Sealed this  
Sixteenth Day of December, 2014

Michelle K. Lee  
*Deputy Director of the United States Patent and Trademark Office*